United States Patent
Hiddessen et al.

(10) Patent No.: US 9,914,957 B2
(45) Date of Patent: Mar. 13, 2018

(54) DEVICES, SYSTEMS AND METHODS FOR THERMAL CONTROL OF DROPLET DETECTION

(71) Applicant: Bio-Rad Laboratories, Inc., Hercules, CA (US)

(72) Inventors: Amy L. Hiddessen, Dublin, CA (US); Erin Rae Chia, Berkeley, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 234 days.

(21) Appl. No.: 14/185,744

(22) Filed: Feb. 20, 2014

(65) Prior Publication Data
US 2015/0017648 A1    Jan. 15, 2015

Related U.S. Application Data

(60) Provisional application No. 61/768,369, filed on Feb. 22, 2013.

(51) Int. Cl.
| | | |
|---|---|---|
| C12Q 1/68 | (2006.01) | |
| B01L 7/00 | (2006.01) | |
| G01N 21/64 | (2006.01) | |
| B01L 3/00 | (2006.01) | |

(52) U.S. Cl.
CPC ...... *C12Q 1/6806* (2013.01); *B01L 3/502784* (2013.01); *B01L 7/525* (2013.01); *C12Q 1/6844* (2013.01); *G01N 21/6486* (2013.01); *B01L 3/502715* (2013.01); *B01L 2300/0816* (2013.01); *B01L 2300/0838* (2013.01); *B01L 2300/1822* (2013.01); *B01L 2300/1827* (2013.01); *B01L 2300/1872* (2013.01); *G01N 2201/06113* (2013.01)

(58) Field of Classification Search
None
See application file for complete search history.

(56) References Cited

U.S. PATENT DOCUMENTS

| | | | |
|---|---|---|---|
| 2006/0257893 A1 | 11/2006 | Takahashi et al. | |
| 2008/0280331 A1 | 11/2008 | Davies et al. | |
| 2010/0137163 A1* | 6/2010 | Link | B01F 13/0071 506/16 |
| 2011/0217712 A1* | 9/2011 | Hiddessen | C12Q 1/6846 435/6.12 |
| 2012/0302448 A1 | 11/2012 | Hutchison et al. | |

FOREIGN PATENT DOCUMENTS

| | | |
|---|---|---|
| WO | WO 2007/081386 A2 | 7/2007 |
| WO | WO 2011/020011 A2 | 2/2011 |

OTHER PUBLICATIONS

Guttenberg, Z. et al. Planar chip device for PCR and hybridization with surface acoustic wave pump. Lab on Cip, vol. 5, p. 308-317, 2005.*
Schaerli, Y. et al. Continuous-flow polymerase chain reaction of single-copy DNA in microfluidic microdroplets. Anal. Chem., vol. 81, p. 302-306, 2009.*
Brouzes, et al. Droplet microfluidic technology for single-cell high-throughput screening. Proc Natl Acad Sci U S A. Aug. 25, 2009;106(34):14195-200.
International search report and written opinion dated Jun. 26, 2014 for PCT/US2014/017492.

* cited by examiner

Primary Examiner — Prabha Chunduru
(74) Attorney, Agent, or Firm — Kolisch Hartwell, P.C.

(57) ABSTRACT

A droplet detection system comprises a first channel in fluid communication with a carrier fluid reservoir and a second channel in fluid communication with a sample reservoir. The first channel and second channel can meet at an intersection. The sample reservoir can include a sample or partition thereof. During use, an emulsion comprising one or more droplets can be generated at the intersection. The emulsion flows from the intersection along a detection channel to a collection reservoir. A detection assembly that is coupled to at least a portion of the detection channel is configured to detect a signal from the one or more droplets. An energy providing member can be in thermal communication with at least one of the carrier fluid reservoir, the sample reservoir, the intersection, the detection channel and the detection assembly. The energy providing member is configured to transfer energy to the emulsion.

9 Claims, 8 Drawing Sheets

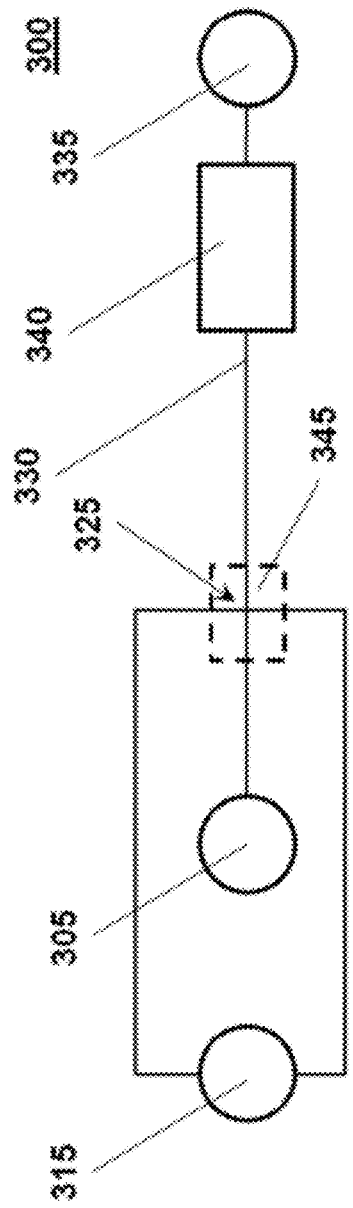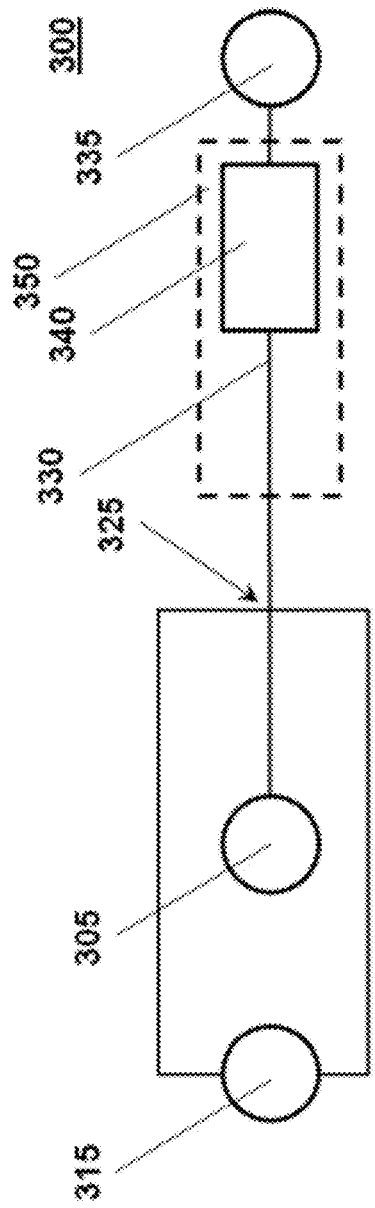

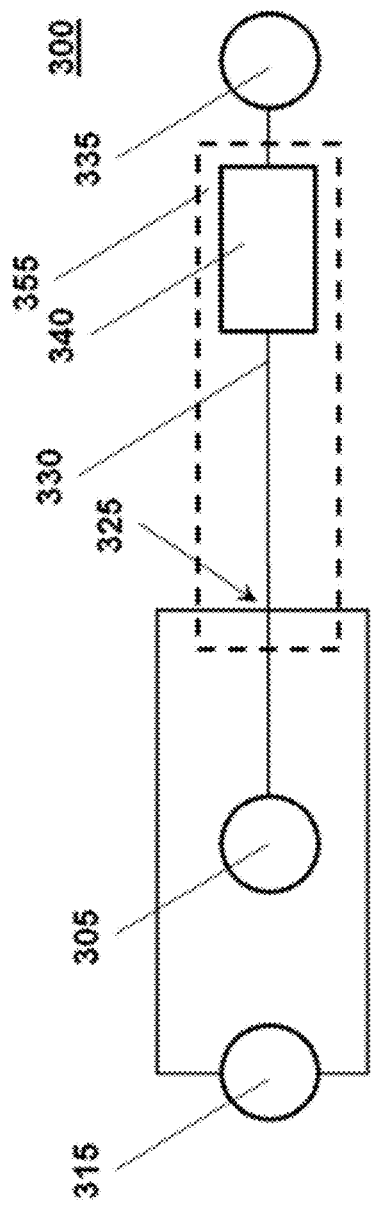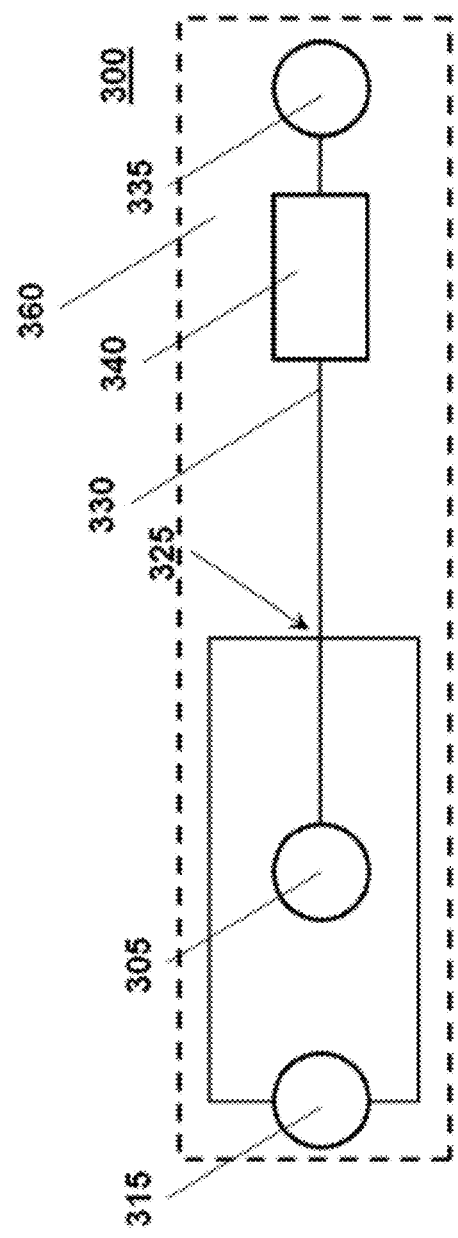

DEVICES, SYSTEMS AND METHODS FOR THERMAL CONTROL OF DROPLET DETECTION

CROSS-REFERENCE

This application claims the benefit of U.S. Provisional Patent Application Ser. No. 61/768,369, filed Feb. 22, 2013, which is incorporated herein by reference in its entirety.

BACKGROUND

Assays can be procedures for determining the presence, quantity, activity, and/or other properties or characteristics of components in a sample. In some cases, the samples to be assayed are complex, the components of interest within the samples—e.g., a nucleic acid, an enzyme, a virus, a bacterium—are only minor constituents of the samples, and the results of the assays are required quickly and/or for many samples.

Some current systems perform assays with the aid of droplets generated in drop generators. Often, the droplet generators work by partitioning a sample into multiple droplets. The sample may be an aqueous sample that is contacted with a stream of oil fluid in such a way as to form a disperse phase of aqueous droplets in a continuous oil phase. In such systems, droplets with sample partitions may be generated for storage in a droplet storage vessel, in which sample can subsequently be processed (e.g., amplified in the case of PCR) and analyzed. Droplets may then be detected such as by being introduced into a droplet reader. Improved droplet detection mechanisms would be of great benefit to biological and clinical assays that use droplet-based assays.

SUMMARY

This disclosure describes a system for thermally controlled detection of droplets, in some cases for the purpose of controlling at least one property of the droplet itself, or a constituent or property of the internal phase of the droplet, to improved droplet generation and/or droplet detection for improved detection quality and accuracy.

In some embodiments, a fluid flow path of a droplet detector is under thermal control. Thermal control may be useful for controlling, such as maximizing, the signal detected from a droplet. Thermal control may be used to more optimally control and detect signals from droplets where droplet physical or chemical properties (e.g., material properties, as in droplet stability), or constituents or properties of the aqueous phase within the droplet (e.g. biological reactions, dyes, pH, fluorophores interacting with biomolecules, and/or other signal generating or signal inhibiting factors) may depend on temperature.

In an example, in a polymerase chain reaction (PCR) process, deoxyribonucleic (DNA) or ribonucleic acid (RNA) binding dyes can both bind and intercalate to the specific (intended) PCR product and non-specific (unintended) products (such as, for example, unintended products or primer dimers). This can adversely impact the accuracy with which the specific product is detected, as an emitted signal may be convoluted with signals from both the specific and non-specific products. In some cases, the non-specific products can be hidden from detection by thermal melting of the DNA, depending on their melting point (Tm), which can depend on size, among other factors. Moreover, in some examples, melting of non-specific products may reduce or completely eliminate binding of the intercalating dye. Reduced or eliminated signals from non-specific products may render them distinguishable from intended, specific products.

In some cases, increasing the temperature of the PCR solution can help minimize, or completely eliminate, signals generated by non-specific products and, thus, improve the accuracy of detection.

Systems and methods of the disclosure are readily applicable to droplet chemistries which have heat-induced stabilization mechanisms, such as a skin.

Systems and methods provided herein can enable improved consistency in droplet quality across experimental setups and/or droplet detectors. In some cases, systems provided herein enable reduced variability among droplet detectors—two droplets having the same sample can be similarly detected in two separate droplet detectors. The disclosure provides for a system having a low coefficient of variation (CV), such as less than 20%, 15%, 10%, 5%, 4%, 3%, 2%, 1%, 0.1%, or less.

An aspect of the present disclosure provides a device for sample detection. The device comprises a first channel in fluid communication with a carrier fluid reservoir and a second channel in fluid communication with a sample reservoir. The carrier fluid reservoir can comprise a carrier fluid and the sample reservoir can comprise a sample or partition thereof. In some cases, the sample reservoir comprises one or more droplets, each comprising a sample or partition thereof. The first channel and second channel can meet at an intersection. The intersection is upstream of a detection channel. During use, the one or more droplets flow from the intersection along the detection channel to a collection reservoir. The device further comprises a detection assembly in optical communication with at least a portion of the detection channel, the detection assembly configured or adapted to detect an electromagnetic signal from the one or more droplets. The detection assembly further comprises an energy providing member in thermal communication with at least one of (i) the carrier fluid reservoir, (ii) the sample reservoir, (iii) the first channel, (iv) the second channel, (v) the intersection and (iv) at least a portion of the detection channel, wherein the energy providing member is adapted to transfer energy to the carrier fluid and the one or more droplets. In some cases, the at least portion of the detection channel does not include sample amplification.

A sample reservoir can comprise a sample, multiple samples, or a partition of a sample. In such a case, one or more droplets comprising a sample or partition thereof can be formed at the intersection. As an alternative, the sample reservoir can comprise the one or more droplets. During use, the one or more droplets flow from the sample reservoir to the intersection, at which point an emulsion comprising the one or more droplets is formed.

Another aspect of the present disclosure provides a device for sample detection. The device comprises a channel in fluid communication with an emulsion source, wherein the emulsion source provides an emulsion that flows along the channel, and wherein the emulsion comprises at least one droplet comprising a sample or partition thereof. The device can further comprise a detection assembly in optical communication with at least a portion of the channel, wherein the detection assembly is adapted to detect an electromagnetic signal from the at least one droplet. The device can further comprises an energy providing member directly adjacent to the portion of the channel that is in optical communication with the detection assembly, wherein the energy providing member is adapted to transfer energy to the emulsion, and wherein the at least the portion of the detection channel does not include sample amplification.

Another aspect of the present disclosure provides a device for sample detection. The device comprises a first channel in fluid communication with a carrier fluid reservoir and a second channel in fluid communication with a sample reservoir. The first channel, second channel and detection channel meet at an intersection. The droplet can have a sample or partition thereof. The droplet flows from the intersection along a detection channel to a collection reservoir. In some cases, the droplet is generated at the intersection. As an alternative the droplet flows from the sample reservoir and is included in an emulsion at the intersection. The device can further comprise a detection assembly coupled to at least a portion of the detection channel. The detection assembly can be adapted to detect a signal from the droplet. The device can further comprise one or more energy providing members, wherein an individual energy providing member is in thermal communication with at least one of (i) the carrier fluid reservoir, (ii) the sample reservoir, (iii) the intersection, (iv) the first channel, (v) the second channel, (vi) at least a portion of the detection channel and (vii) the detection assembly. In some cases, the least portion of the detection channel does not include sample amplification.

Another aspect of the present disclosure provides a device for sample detection, comprising a channel in fluid communication with a sample reservoir and a collection reservoir, wherein the sample reservoir comprises one or more droplets each comprising a sample or a partition thereof, and wherein the one or more droplets flow along the channel to the collection reservoir. The device can further comprise a detection assembly in optical communication with at least a portion of the channel. The detection assembly can be adapted to detect a signal from the one or more droplets. The device further comprises an energy providing member in thermal communication with at least one of (i) the sample reservoir and (ii) the channel, wherein the energy providing member is adapted to transfer energy to the one or more droplets. In some situations, the least portion of the channel does not include sample amplification.

Another aspect of the present disclosure provides a method for analyzing a sample, comprising flowing an emulsion comprising one or more droplets in a carrier fluid along a detection channel to a collection reservoir, wherein a given droplet among the one or more droplets comprises the sample or a partition thereof. Next, upon the flow of the emulsion along the detection channel, an optical signal from the droplets can be detected in a detection assembly in optical communication with at least a portion of the detection channel. In some cases, (i) the carrier fluid can be energized prior to flowing the emulsion along the detection channel, (ii) the emulsion can be energized after generating the emulsion and prior to detecting an optical signal, and/or (iii) the emulsion can be energized along at least a portion of the detection channel. In some situations, the method comprises (i) and (ii), (ii) and (iii), (i) and (iii), or all of (i)-(iii). In some situations, the least portion of the detection channel does not include sample amplification.

Another aspect of the present disclosure provides a method for detecting a nucleic acid in a sample. The method comprises providing a sample comprising a plurality of partitions, wherein at least one of the partitions comprises an amplified nucleic acid, and wherein the temperature of the plurality of partition is at least about 50° C. Next, an optical signal from at least one of the plurality of partitions can be detected. The optical signal can be correlated with an amount of the nucleic acid.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also referred to as "Figures" or "FIGS.") of which:

FIGS. 3A-3D schematically illustrate droplet detection systems comprising various configurations of energy application zones;

DETAILED DESCRIPTION

Figure 1:
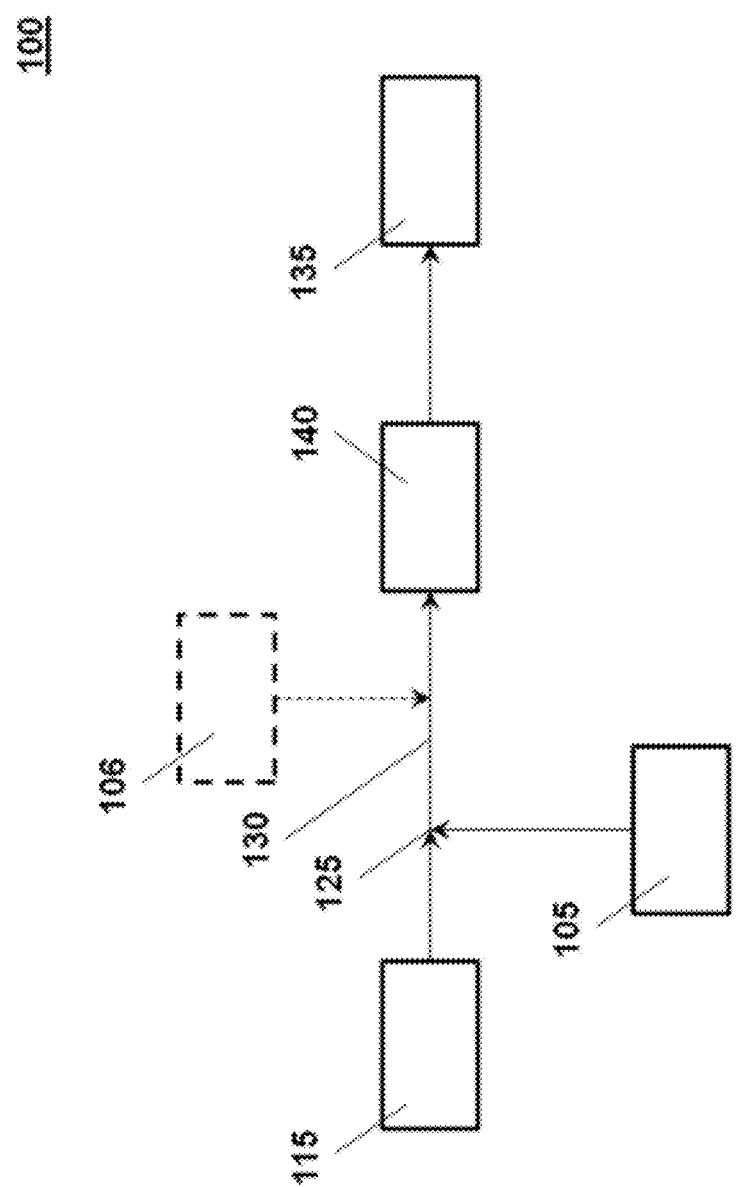
FIG. 1 schematically illustrates a droplet detection system of the disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention.

The term "channel," as used herein, generally refers to a flow path for conveying a fluid, which may include an emulsion, from one point to another.

The term "downstream" and "upstream," as used herein, generally refer to the position of a species, such as a droplet, along a system or device(s), such as along a fluid flow path in a droplet generator. A first droplet downstream of a second droplet can be further along a fluid flow path than the second droplet, either in the same device or a separate device. The devices may or may not be connected, such as by a flow path. The second droplet in such a case is upstream of the first droplet.

The term "emulsion," as used herein, generally refers to a mixture of two or more fluids that are normally immiscible. An emulsion can include a first phase in a second phase, such as an aqueous phase in an oil phase. In some cases, an emulsion includes more than two phases. It may also include multiple emulsions. Moreover, in some examples, an emulsion may include particulates that may function to stabilize the emulsion and/or function as a coating (e.g., gel-like coating), such as a droplet skin.

Devices and Systems for Sample Detection

An aspect of the disclosure provides a system for sample detection. The system can be configured to detect a sample or sample partition within one or more droplets directed through a fluid flow path of the system. In some situations, energy is applied to one or more droplets to improve sample detection.

Droplets may be directed through a fluid flow path as an emulsion. As an alternative, such as if the droplets have substantially solid surfaces (e.g., skins), the droplets may be directed through a fluid flow path as a slurry.

In some examples, energy applied to the one or more droplets improves sample detection by minimizing, if not eliminating droplet coalescence. Applied energy may also improve sample detection by reducing, if not eliminating, the signal generated by non-specific targets. Energy applied to an individual droplet may in some cases neutralize the excitation capability of an unintended product while not affecting the excitation capability of an intended product.

A system for sample detection may comprise a first channel in fluid communication with a carrier fluid reservoir and a second channel in fluid communication with a sample reservoir. The first channel and second channel meet at an intersection that receives a sample from the sample reservoir and a carrier fluid (e.g., oil) from the carrier fluid reservoir and generates an emulsion that includes one or more droplets. Alternatively, an emulsion may already be formed in the sample reservoir and/or carrier fluid reservoir. In some cases, the sample in the sample reservoir may be in the form of an emulsion or a slurry. The emulsion flows along a detection channel to a collection reservoir. Flow of the emulsion is facilitated with the aid of negative pressure (or vacuum) provided at a point downstream of the intersection and/or positive pressure provided in one or more of the collection reservoir, the carrier fluid reservoir and the sample reservoir.

In some examples, the intersection is a singulator that receives a carrier fluid (e.g., focusing fluid) and droplets from a sample reservoir comprising the droplets. The singulator can separate droplets prior to detection by a detection assembly.

The system may further comprise a detection assembly in optical communication with at least a portion of the detection channel. The detection assembly is configured to detect a signal from the droplet, such as an optical signal that may be generated upon exposure of the droplet to a source of excitation energy (e.g., excitation light). The detection assembly can include an energy providing member (e.g., heating member) in thermal communication with at least a portion of the detection channel. The heating member transfers heat to the emulsion.

Samples in the sample reservoir may be provided in droplets. In such a case, the sample reservoir provides droplets to the intersection. A droplet can include a sample partition, such as a fraction of a sample. In some cases the sample partition is prepared as a reaction mixture and amplified, such as with the aid of polymerase chain reaction (PCR).

Droplets collectively or each can include one or more dyes. In some examples, a droplet can include at least 2, 3, 4, 5, 6, 7, 8, 9, 10, 15, 20, 30, or 40 different dyes. In some embodiments, droplets can be of at least two types, such as two or more types of test droplets, test droplets and calibration droplets, or test droplets and control droplets, among others. In some embodiments, the two or more types of droplets may be distinguishable based on distinct temporal positions of the droplet types in a flow stream (or distinct times of exit from the intersection, the presence of respective distinct dyes in the droplet types, distinguishable signal intensities of the same dye (or different dyes), or a combination thereof.

In some situations, a droplet flows through a fluid flow path as an emulsion, which may be characterized by the predominant liquid compound or type of liquid compound in separate phases. For example, the phases may be an oil phase and an aqueous phase. In some cases, one or more of the phases may be a fluorous phase. In some situations, the predominant fluids in the emulsion are aqueous and oil. Oil is any liquid compound or mixture of liquid compounds that is immiscible with water that may be miscible with organic species such as alcohols and ethers. Oil may, for example, comprise a carbon and/or hydrogen content, may be non-polar, and/or may be flammable. In some examples, oil may also have a high content of fluorine, silicon, oxygen, or any combination thereof, among others. For example, any of the emulsions disclosed herein may be water-in-oil (W/O) emulsion, i.e., aqueous droplets in a continuous oil phase. Conversely, any of the emulsions disclosed herein may be oil-in-water (O/W) emulsions. This disclosure also provides multiple emulsions. For example, aqueous droplets may be enveloped by a layer of oil and flow within an aqueous continuous phase. The oil may, for example, be or include at least one of silicone oil, mineral oil, fluorocarbon oil, vegetable oil, or a combination thereof, among others. Any other suitable components may be present in any of the emulsion phases, such as at least one surfactant, reagent, sample (i.e., partitions thereof), other additive, label, particles, or any combination thereof.

Systems provided herein may be configured for use with various types of samples, such as nucleic acid samples, proteomic samples, small-molecule samples, and cellular samples. Nucleic acid samples can include deoxyribonucleic acid (DNA) and ribonucleic acid (RNA), including variants thereof (e.g., circular DNA or RNA, single-stranded DNA or RNA).

In the detection assembly, signals, such as optical (e.g., fluorescence) signals, can be detected from the droplets. The signals may include test signals, calibration signals, control signals, reference signals, or any combination thereof. In some embodiments, test signals and control signals may indicate respectively whether amplification of a test nucleic acid target and a control nucleic acid target occurred in individual droplets. In some embodiments, the detection assembly includes a detection system for collecting light and, in some cases, providing excitation energy, such as excitation light. The wavelength of excitation light can be selected to induce excitation within a droplet.

Detection in the detection assembly may include (a) exciting a dye with the aid of excitation light and (b) detecting emitted light from the dye. In some embodiments, detection in the detection assembly includes (a) exciting multiple dyes with of the aid of excitation light and (b) detecting emitted light from the dyes at least substantially independently from one another in one or more detector channels.

The system for sample detection may further include an energy providing device (or member) for coupling energy to a droplet at or downstream of one or more of (i) the intersection, (ii) at least a portion of the detection channel, (iii) the sample reservoir, (iv) the carrier fluid reservoir, (v) the first channel and (vi) the second channel. In some cases, energy is coupled to the collection reservoir, which can be a waste reservoir. In some cases, the energy providing device transfers energy to an individual droplet at the intersection and/or as the droplet moves along the detection channel to the collection reservoir.

The energy providing device can be an energy source that is coupled to (e.g., in thermal communication with) a fluid flow path of the system, including the intersection, at least a portion of the detection channel, the carrier fluid reservoir and/or the sample reservoir. In some cases, the energy providing device is a heat source that is thermally coupled to the fluid flow path. In some cases, the energy providing device includes a heating device in thermal communication with the fluid flow path. Alternatively, the energy providing device can be a source of electromagnetic radiation, such as such as ultraviolet (UV), infrared (IR), or visible light. In an example, the energy providing device is a laser. The energy providing device can be removable or integrated into the system.

In some cases, the energy providing device is a heating element. The heating element can be a resistive heating element, in some cases comprising one or more elemental metals selected from Ta, Ti and W. The heating element can have a composition and dimension that is selected to provide a desired or otherwise predetermined heating rate (power) to heat droplets flowing through the fluid flow path, including the intersection, at least a portion of the detection channel, the carrier fluid reservoir and/or the sample reservoir. In some cases, the heating element is thermally coupled to fluid flow path with the aid of a heat conductor, such as, for example, a foil comprising copper or a copper alloy.

The heating element may include one or more thermoelectric devices thermally coupled to the fluid flow path. The thermoelectric device can be selected to provide a desired heating rate to droplets flowing through the fluid flow path.

The system may transfer energy to an individual droplet to neutralize the excitation capability of an unintended product while not affecting the excitation capability of an intended product. As such, the system may improve droplet detection.

In some cases, the system transfers energy to an individual droplet or an emulsion having the droplet in order to avoid or mitigate deterioration of temperature sensitive reagents. Temperature control in some cases can aid in regulating one or more properties of an individual droplet or emulsion, such as the viscosity of a droplet and/or emulsion, or the density of a droplet and/or emulsion.

Temperature control may provide other uses or benefits. The system may transfer energy to an individual droplet or an emulsion having the droplet in order to avoid or mitigate deterioration of temperature sensitive reagents. Temperature control in some cases can aid in regulating one or more properties of an individual droplet or emulsion, such as the viscosity of a droplet and/or emulsion, or the density of a droplet and/or emulsion.

In some embodiments, the system transfers heat to an individual droplet to form a skin around the droplet. Energy may be provided to the droplet before the intersection and/or after the intersection but before the detection assembly. In some embodiments, the droplet contains a protein, such as bovine serum albumin, which can form a component of the skin. In some embodiments, the droplet contains a polymer or other molecule that cross-links upon exposure to electromagnetic radiation to form a component of the skin. The electromagnetic radiation may be UV radiation. For instance, the system may transfer energy to an individual droplet to form a skin around the droplet. A skin can be formed upon thermally-induced cross-linking, for instance, or by cross-linking upon exposure of a droplet to electromagnetic radiation having a frequency (or energy) capable of inducing cross-linking. The skin can have an area compressibility modulus between about 0.01 mN/meter and 10000 mN/meter at a temperature of about 25° C.

As an alternative, droplets in the sample reservoir include skins. The skins may be formed by applying energy to the droplets in the sample reservoir, or at a point in which the droplets are formed, such as in a droplet generator.

The system may further include a third channel in fluid communication with the carrier fluid reservoir. The third channel may meet with the first and second channels at the intersection.

In some examples, one or more samples from the sample reservoir is directed to the intersection in droplets and brought in contact with a carrier fluid from the carrier fluid reservoir to form an emulsion having the droplets. Alternatively, the sample reservoir may supply a pre-formed emulsion of sample droplets. An individual droplet may include a sample or sample partition. The droplets flow along the detection channel as an emulsion that may be made up of a plurality of phases, such as a first phase and a second phase. The first and second phases may be separated by an outer boundary of the droplet, such as a skin.

The droplets, skin, or both may be formed prior to forming the emulsion. In some examples, a droplet is formed in a separate or integrated droplet generator. The droplet may include a skin, which may also be formed in the droplet generator.

In some embodiments, the droplet detector is included in a housing having one or more droplet detectors. The housing can include a plurality of droplet detectors for parallel detection, which can aid in maximizing detection efficiency—e.g., a plurality of samples can be detected in parallel, thereby reducing droplet detection time.

In some embodiments, the system includes a pressure source for facilitating the flow of droplets from the intersection to the collection reservoir. The pressure source can be a source of positive pressure operatively coupled to the carrier fluid and/or sample reservoir, or a source of negative pressure (i.e., vacuum) operatively coupled to the fluid flow path, such as by way of the collection reservoir. The source of positive pressure can be a compressor or a pressurized fluid, such as a pressurized gas (e.g., pressurized air). The source of negative pressure can be a pumping system comprising one or more pumps, such as mechanical pumps.

The system may be configured for nucleic acid amplification, such as polymerase chain reaction (PCR). In some embodiments, an energy providing device is used to raise the temperature of droplets provided at the intersection to initiate amplification. The system can thermally cycle the temperature of the droplets, from a low temperature to a high temperature, and in some cases to a low temperature with the aid of cooling. Cooling can be implemented with the aid of heat fins, for instance, or a cooling system, such as a thermoelectric cooling system.

In some situations, the energy providing device comprises an interface plate that is formed of a metallic material. During sample processing, the droplet detector can rest adjacent to the interface plate. Such configuration can aid in transferring heat to the droplets upon formation and/or flow through the fluid flow path. The interface plate can be coupled to a source of energy, such as a resistive heating element that can be integrated in the system. In some embodiments, the energy source is external to the system. Examples of energy sources include but are not limited to a resistive heating element, such as an integrated resistive heating element, a water bath, or a thermoelectric heating element, such as a Peltier device.

The energy providing device can be integrated in the droplet detector, or separate from the droplet detector. In some cases, the energy providing device is removable from the droplet detector. In an example, the energy providing device is a resistive heating element that is formed in a housing of the droplet detector. Power (heat per unit time) can be generated by the heating element upon the application of electricity to the electrodes of the heating element that are electrically coupled to power terminals of a heating system, as may be provided in the droplet detector.

In some situations, the system includes a detection assembly in fluid communication with the fluid flow path. The detection assembly may be situated along at least a portion of the detection channel between the intersection and the collection reservoir. The detection assembly can be configured to detect signals from droplets in the fluid flow path, such as upon flowing through the detection channel. The detection assembly can include an optical sensor or other electronic detector that is sensitive to a select frequency of light. The sensor can be adapted to detect fluorescent emission, for example. In some cases, the detection assembly can include an excitation source, such as a light source that is adapted to induce fluorescence in the fluid. One or more optical elements (e.g., mirrors, lenses) can be provided to direct light emitted from the fluid to the detection assembly, and/or to direct light from a light source to the fluid.

In some examples, a device for sample detection comprises a first channel in fluid communication with a carrier fluid reservoir and a second channel in fluid communication with a sample reservoir. The first channel and second channel can meet at an intersection to form an emulsion upon the carrier fluid coming in contact with the sample. Alternatively, an emulsion comprising droplets may already be formed in the sample reservoir and/or carrier fluid reservoir. The emulsion can include droplets containing a sample from the sample reservoir. In some cases, the emulsion may be formed separately and/or off-line and be provided to the device (e.g., by pipetting). The sample reservoir may comprise the droplet(s).

The device may further include a detection channel leading from the intersection to a collection reservoir. The emulsion may flow along the detection channel to the collection reservoir. A detection assembly may be in optical communication with at least a portion of the detection channel. The detection assembly may be adapted to detect an electromagnetic (i.e., optical) signal from the droplet. In some instances, at least a portion of the detection channel includes sample amplification (e.g., PCR amplification of a nucleic acid).

In other examples, a detection assembly may be arranged in a stop-flow configuration. In such a configuration, droplets are captured in non-flow conditions and detected. For example, droplets may be individually arrayed on a slide or each entered into an individual well of a multi-well plate. The slide or multi-well plate comprising the droplets may then be brought into communication with a detection assembly for detection of the droplets.

Emulsions and/or droplets may be maintained at a constant temperature in the devices, systems, and methods described herein. Constant temperature can be provided by heating the droplets and/or emulsions and may be advantageous for obtaining an accurate signal in an assay. A constant temperature may vary by less than about 10° C., less than about 1° C., less than about 0.5° C., or less than about 0.1° C. Systems of the disclosure can have a coefficient of variation (CV) less than about 20%, 15%, 10%, 5%, 4%, 3%, 2%, 1%, 0.1%, or less.

Devices and systems of the disclosure may include an energy providing (or application) member in thermal communication with at least one of the carrier fluid reservoir, the sample reservoir, the intersection, and the detection channel. The energy providing member is adapted to transfer energy to the emulsion and/or droplets.

The energy providing member may provide thermal energy (e.g., heat), electromagnetic energy, electrical energy, chemical energy, mechanical energy, or any combination thereof. In some instances, the energy providing member is configured to maintain a droplet at a constant temperature. The energy providing member may provide energy that is converted into thermal energy. In some embodiments, energy providing member comprises a heat sink adjacent to a thermoelectric device. The heat sink can include a plurality of heat fins. The energy providing member can comprise a resistive heating element. The energy providing member may also be in thermal communication with a portion of the detection channel.

The detection assembly may be disposed along the detection channel. The detection assembly may detect any suitable signal from the droplets. In some cases, the detection assembly includes confocal optics. The detection assembly may be in optical communication with a source of energy (e.g., visible light).

The device may further comprise a pressure source for facilitating the flow of the droplet to the collection reservoir. The pressure source may include a source of positive pressure or negative pressure.

The device may further comprise a controller in communication with the detection assembly. The controller can include a computer processor programmed to estimate the presence or absence of a nucleic acid target in the sample.

In some examples, an energy providing member provides thermal energy to heat the one or more droplets of the emulsion, which can provide droplet stabilization. As a consequence, the droplets may be more resistant to coalescence after stabilization than before stabilization. Transferring thermal energy may form a skin around the droplet(s). As an alternative, the droplets may include skins before thermal energy is provided.

Reference will now be made to the figures, wherein like numerals refer to like parts throughout. It will be appreciated that the figures are not necessarily drawn to scale.

FIG. 1 schematically illustrates a droplet detection system (or droplet detector) 100 comprising a sample reservoir 105 and a carrier fluid reservoir 115 that meet at an intersection 125. In some examples, the droplet detector is adapted or otherwise configured to detect a signal (e.g., optical signal) emanating from one or more droplets.

During use, an emulsion may be formed at the intersection 125 or may already be formed in sample reservoir 105. The sample reservoir 105 may provide samples or sample partitions in individual droplets. The individual droplets may be generated in a droplet generator. In some examples, a flow modulating or enhancing material may be provided from a reservoir 106. The emulsion flows directly into a detection channel 130. Droplets and/or emulsions can be collected in a collection reservoir 135.

A detection assembly 140 can be provided along the detection channel 130 to aid in detecting one or more samples or sample partitions in the droplets. The detection assembly 140 may include one or more components (e.g., optics, sensors) for detecting a signal emanating from a droplet. In some cases, the detection system includes an excitation light source and a detector for detecting light emitted from a droplet following excitation. The detection assembly 140 may be coupled to one or more detection regions of the detection channel 130 (e.g., through a channel or capillary). In some examples, the one or more detection regions of the detection channel 130 include windows for permitting an electromagnetic (or optical) signal to reach a fluid (e.g., emulsion), that may include one or more droplets, flowing through the detection channel. The detection assembly 140 may be a droplet detector, as described in, for example, U.S. Patent Publication No. 2010/0173394 to Colston et al. ("Droplet-based assay system"), which is entirely incorporated herein by reference for all purposes.

The sample reservoir 105 can include droplets having samples or sample partition therein. Each droplet can include a nucleic acid sample or portion thereof, and a species that is configured to be excited by a source of excitation energy or stimulus. Some examples of species that are configured to be excited include dyes, such as intercalating dyes or labeled probes, such as labeled oligonucleotide probes. Examples of intercalating dyes are ethidium bromide, SYBR Green™, SYBR Gold™, 4',6-diamidino-2-phenylindole (DAPI), or combinations thereof. A labeled oligonucleotide probe may be, for example, a TaqMan probe, wherein quenched fluorophores labels bound to the oligonucleotide probe are released by the exonuclease activity of a DNA polymerase (e.g., Taq polymerase) after probe binding to its target. Release of the fluorophore from quenching may result in its detection. Moreover, a droplet may have a skin on an outer portion of the droplet. The skin may aid in providing droplet stability during detection.

An individual droplet can include a sample or sample partition. The sample or sample partition may be a nucleic acid sample (e.g., DNA or RNA sample), which may have been amplified, such as with the aid of polymerase chain reaction (PCR). As an alternative, the individual droplet may include reagents (e.g., primers, polymerase(s), nucleic acids) for nucleic acid amplification.

Figure 2:
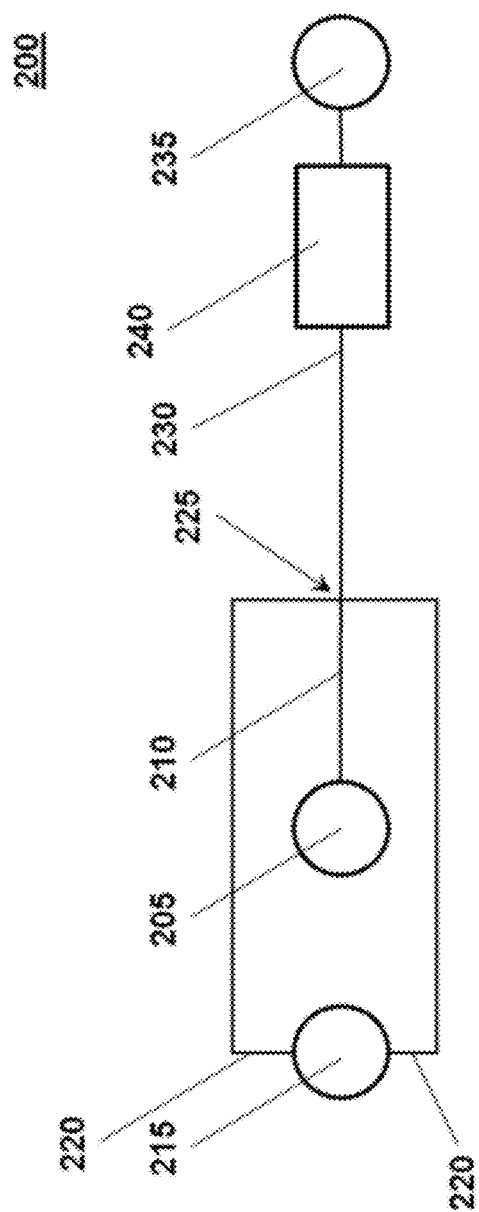
FIG. 2 schematically illustrates another droplet detection system of the disclosure.

FIG. 2 shows an example droplet detection system 200. The detection system 200 includes a sample reservoir 205 in fluid communication with a sample channel 210 and a carrier fluid reservoir 215 in fluid communication with carrier fluid channels 220. The sample channel 210 and carrier fluid channels 220 meet at an intersection 225. During operation, a carrier fluid (e.g., oil) from the carrier fluid reservoir 215 is directed through the carrier fluid channels 220 to the intersection 225, and a sample (e.g., a sample in a droplet) from the sample reservoir 205 is directed through the sample channel 210 to the intersection 225. The carrier fluid and the sample may be directed with the aid of positive and/or negative pressure. At the intersection 225, an emulsion may be generated comprising the carrier fluid and a sample or sample partition, such as one or more droplets each comprising a sample or sample partition. Alternatively, an emulsion may already be formed in sample reservoir 205 prior to sample arrival at intersection 225. In some examples, the emulsion comprises a droplet in the carrier fluid. An emulsion then flows in a detection channel 230 from the intersection 225 to a collection reservoir 235. A detection assembly 240 along the detection channel 230 detects droplets in the emulsion as the emulsion flows from the intersection 225 to the collection reservoir 235. The detection assembly 240 may be a droplet detector, as described elsewhere herein.

The sample channel 210 may be perpendicular or non-perpendicular to the carrier fluid channels 220. In some cases, a carrier fluid channel 220 is at an angle from about 10° to 90°, or 25° to 80°, or 40° to 70° with respect to the sample channel 210, or at least about 10°, 15°, 20°, 25°, 30°, 40°, 50°, 60°, 70°, 80°, or 85° with respect to the sample channel 210.

Figure 6:
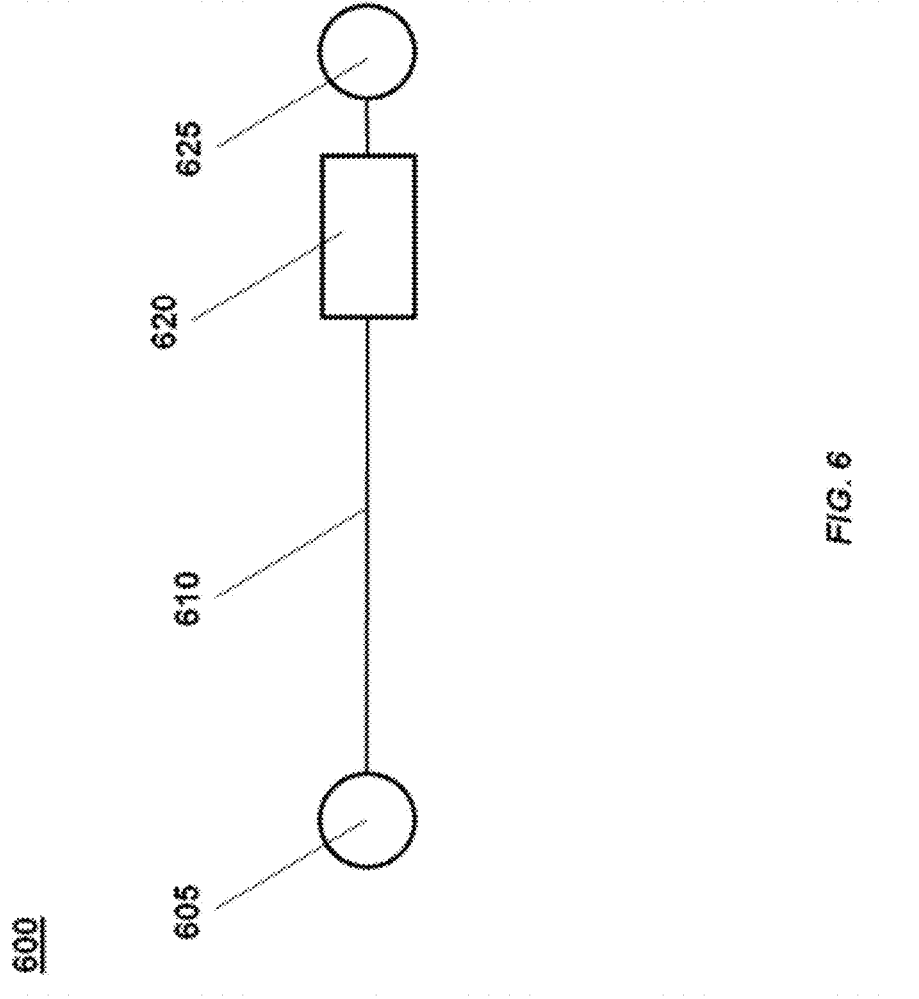
FIG. 6 schematically illustrates a droplet detection system.

FIG. 6 shows an example of a droplet detection system 600. The detection system 600 includes a sample reservoir 605 in fluid communication with a sample channel 610. During operation, a sample (e.g., a sample in a droplet or an emulsion comprising droplets comprising sample) from the sample reservoir 605 is directed through the detection channel 610 to a collection reservoir 625. A detection assembly 620 along the detection channel 610 detects droplets in the sample as the sample flows from the sample reservoir 605 to the collection reservoir 625. The detection assembly 620 may be a droplet detector, as described elsewhere herein.

The systems of FIGS. 1, 2, and 6 may be integrated with a droplet generator, such as droplet generators described in U.S. Patent Publication No. 2010/0173394 to Colston et al. ("Droplet-based assay system"), which is entirely incorporated herein by reference for all purposes.

In some cases, an associated droplet generator may be separately situated in relation to a droplet detector. In other cases, the droplet generator and the droplet detector are part of the same system and may be in fluid communication with one another. For example, one or both of the sample reservoir 205 and the carrier fluid reservoir 215 of the system 200 of FIG. 2 may be precluded or modified to account for a device having a droplet generator upstream of the system of FIG. 2.

The systems of FIGS. 1 and 2 can be formed in a single-piece or multi-piece substrate. The substrate can include at least 1, 2, 3, 4, 5, 6, 7, 8, 9, or 10 droplet detectors, each of which may be as described in FIGS. 1 and 2.

A droplet detection system may include a fluid focusing mechanism comprising a sample (or droplet) channel and a carrier fluid channel that meet at an intersection. The intersection may be configured to separate sample-containing droplets from each other by a given distance. This mechanism may be used, for example, to separate droplets prior to transferring them to a detection assembly comprising a detector. At the intersection, the carrier fluid may mix with a droplet. The droplet may then flow along a detection channel as an emulsion. The flow may be directed away from the intersection at a flow rate that may be a function of at least the flow rate of the carrier fluid. The droplet may flow along the detection channel to a detection zone that is coupled to a detection assembly.

A droplet detection system may include an energy providing (or energy application) device for providing energy to a droplet to provide droplet stability. Energy may be provided to the droplet by (i) providing energy to the droplet in the sample reservoir or in an outlet channel in fluid communication with the sample reservoir, (ii) providing energy to the carrier fluid in the carrier fluid reservoir or in an outlet channel in fluid communication with the carrier fluid reservoir, (iii) providing energy to the droplet and the carrier fluid at the intersection, (iv) providing energy to the droplet and the carrier fluid along at least a portion of the detection channel, and/or (v) providing energy to the droplet and the carrier fluid in the detection assembly.

Energy may be provided to the droplet with the aid of an energy providing device. The energy providing device can be coupled to the droplet detector through one or more energy application zones. In an example, a droplet detector includes one or more heating zones for applying thermal energy to a droplet. The heating zones can be isolated from one another with the aid of insulators, such as an insulating polymeric material, or cooling zones.

An energy application zone can be coupled to one or more of the intersection, the detection channel, the collection reservoir, the sample reservoir and the carrier fluid reservoir. In some cases, a droplet detector can include a plurality of energy application zones, with each zone coupled to at least one of the intersection point, the detection channel, the collection reservoir, the sample reservoir and the carrier fluid reservoir.

In some situations, an energy application zone is coupled to the intersection. In some cases, this can aid in applying energy to a droplet at the moment an emulsion comprising the droplet is formed. In some cases, the emulsion and the droplet are contacted with energy for a given period of time at the intersection, such as, e.g., a period of at least about 0.001 seconds, 0.01 seconds, 0.1 seconds, 0.5 seconds, 1 second, 2 seconds, 3 seconds, 4 seconds, 5 seconds, 10 seconds, 30 seconds, 40 seconds, 50 seconds, 1 minute, 2 minutes, 3 minutes, 4 minutes, 5 minutes, 10 minutes, 30 minutes, or 1 hour. In some cases, the emulsion and the droplet are contacted with energy for a given period of time while the droplet is within any region of the droplet detector, such as, e.g., a period of at least about 0.001, 0.01, 0.1, 0.5, 1, 2, 3, 4, 5, 6, 7, 8, 9, 10, 20, 30, 40, 50 or more seconds, or at least about 1, 2, 3, 4, 5, 10, 20, 30, 40, 50, 60 or more minutes.

In some situations, an energy application zone is coupled to at least a portion of the detection channel. This can aid in applying energy to a droplet between the point an emulsion is formed and the point the droplet is collected in the collection reservoir. In some cases, the droplets are first contacted with the energy in a detection channel for a given period of time, such as at least about 0.001 seconds, 0.01 seconds, 0.1 seconds, 0.5 seconds, 1 second, 2 seconds, 3 seconds, 4 seconds, 5 seconds, 10 seconds, 30 seconds, 1 minutes, 10 minutes, 30 minutes, or 1 hour after formation of the emulsion.

In some examples, energy may be applied to a droplet prior to detection to improve droplet detection. Energy may be applied to a droplet prior to detection to induce or initiate nucleic acid amplification, such as polymerization through polymerase chain reaction (PCR).

An energy application zone may be coupled to the sample reservoir and/or the carrier fluid (e.g., oil) reservoir and/or output channels in fluid communication with either reservoir. Such a configuration can aid in providing energy to the sample and/or the carrier fluid. At least a portion of the energy can be subsequently transferred to an emulsion of droplets that may form at the intersection.

FIGS. 3A-3D illustrate example droplet detection systems comprising energy application zones, as may be used with droplet detection systems provided herein, such as the systems of FIGS. 1 and 2. Energy application zones in the figures are indicated by rectangles with dashed sides. FIG. 3A shows a droplet detection system 300 having a sample reservoir 305, sample channel 310, carrier fluid reservoir 315, carrier fluid channels 320, an intersection 325, detection channel 330, a collection reservoir 335 and a detection assembly 340. At least a portion of the detection channel 330 is coupled to the detection assembly 340. The detection assembly 340 can be, for example, an optical, electrostatic, or electrochemical detector. The detection assembly 340 can be configured to excite one or more dyes in droplets flowing through the detection channel 330 and detecting emission from excited dyes.

The system 300 of FIG. 3A includes an energy application zone 345 coupled to the intersection 325. The energy application zone 345 is in communication (e.g., thermal communication) with an energy source, such as a resistive heater. FIG. 3B shows system 300 having an energy application zone 350 coupled to the detection channel 330 and the detection assembly 340. As an alternative, the energy application zone 350 can be coupled to the detection channel 330 or the detection assembly 340. FIG. 3C shows the system 300 having an energy application zone 355 coupled to the intersection 325, the detection channel 330 and the detection assembly 340. As an alternative, the energy application zone 355 can be coupled to any two of the intersection 325, detection channel 330 and the detection assembly 340. For example, the energy application zone 355 can be coupled to the intersection 325 and the detection assembly 340, or the intersection and the detection channel 330. FIG. 3D shows the system 300 having an energy application zone 360 coupled to the system 300 in its entirety, including the sample reservoir 305, carrier fluid reservoir 315, the intersection 325, the detection channel 330, and the collection reservoir 335. Heating the system 300 can heat the channels of the system 300, including the fluid in the channels. In some examples, the collection reservoir is heated.

The system 300 can include multiple sub-systems, each comprising an intersection 325 and detection channel 330. For instance, multiple detection sub-systems, such as any of those illustrated in FIGS. 3A-3D, may be provided in a parallel configuration. Heating the system 300 can enable the detection sub-systems to be heated simultaneously.

Energy application zones may be coupled to an energy source, such as a source of infrared (IR) light, a resistive heating element or a convective energy source, such as a warm fluid. In an example, the energy application zone 345 of FIG. 3A includes an IR light source that is optical communication with the intersection 325, such as, for example, with the aid of mirrors and focusing optics. In another example, the energy application zone 350 of FIG. 3B includes a resistive heating element in thermal communication with at least a portion of the detection channel 330.

In an example implementation of detection systems with energy providing devices, an emulsion having a plurality of droplets in a carrier fluid (e.g., oil) is formed with the aid of the system 300 of FIG. 3B having the energy application zone 350 along at least a portion of the detection channel 330 and the detection assembly 340. The energy application zone 350 is in thermal communication with a resistive heating element, which includes one or more metals (e.g., tantalum, titanium) in electrical communication with an electrical power source. During use, droplets comprising samples from the sample reservoir 305 and oil from the carrier fluid reservoir 315 are directed to the intersection 325, at which point the droplets come in contact with the carrier fluid to form an emulsion. The emulsion thus formed includes a plurality of droplets, with each droplet including a sample or sample partition. Alternatively, the emulsion may be already be formed upstream of intersection 325, such as, for example, in sample reservoir 305. The sample or sample partition can include an intercalated dye. The droplets then flow through the detection channel 330 to the collection reservoir 335. As the droplets flow along the detection channel 330 from the intersection 325 to the collection reservoir 335, the droplets are heated upon the application of thermal energy from the energy providing member to the energy application zone 350. The droplets, including any samples or samples partitions in the droplets, are detected with the aid of a detection assembly 340 in communication with a portion of the detection channel 330.

An emulsion may be directed to a collection reservoir. The reservoir may contain the emulsion (e.g., droplets plus carrier fluid) and may also contain a volume of air, such as in the headspace of the reservoir.

In some examples, heating droplets can improve droplet detection. For instance, droplets can be heated to increase the ratio of specific target signal to non-specific target signal. A non-specific target includes, but is not limited to, any molecular binding event that is not a nucleic acid base pairing. Non-specific targets may also include primer-dimer pairs. In some examples, droplets can be heated such that the ratio between specific targets and non-specific targets is at least about 1, 1.5, 2, 3, 4, 5, 6, 7, 8, 9, 10, 20, 30, 40, 50, 60, 70, 80, 90, 100, 200, 300, 400, 500, 1000, 2000, 3000, 4000, 5000, 6000, 7000, 8000, 9000, 10,000, 100,000, or 1,000,000.

Droplets may have skins, which may be formed in a droplet generator before the droplet, including a sample in the droplet, is detected with the aid of the detection assembly. In some cases, a droplet with a skin is capable of withstanding shear forces or other mechanical perturbations for a time period of at least about 1 second, 10 seconds, 30 seconds, 1 minute, 10 minutes, 30 minutes, 1 hour, 2 hours, 3 hours, 4 hours, 5 hours, 6 hours, or more.

In some embodiments, a detection channel leading from an intersection to a collection reservoir has a cross section that is circular, triangular, oval, square-like, rectangular, trapezoidal, or pentagonal. The size and/or shape of the cross section can be consistent along the length of the detection channel, or can vary along the length of the detection channel. In some embodiments, the detection channel is linear, curved, angled, planar, non-planar curvilinear (or serpentine), or some combination thereof. A serpentine channel may be planar. Such a serpentine detection channel ("serpentine channel") can increase the residence time of a droplet in a select portion of the detection channel, such as in an energy application zone.

The path of the detection channel can be substantially linear. In some embodiments, the path of the detection channel can comprise one or more meanders. A meander can be a section of fluid flow path that does not take the shortest path between two points. The one or more meanders can be in series, in parallel, or a combination of series and parallel. The meanders can be configured to provide a desired or otherwise predetermined flow resistance, a desired residence time, a desired mixing, or the like. In some examples, a meander can be configured to provide a residence time for an emulsion to equilibrate to a desired or otherwise given temperature. In some examples, a meander can be configured to provide a residence time for an emulsion to incubate for a given time at a given temperature.

In some examples, one or more droplets flow along a detection channel at a flow rate between about 0.5 microliter/minute and 10,000 microliters/minute, or 1 microliter/minute and 5,000 microliters/minute. The flow rate can be computed by the relationship: number of droplets/time*average volume (µl)/droplet. Energy may be provided to the one or more droplets under flow.

The Weber number is a dimensionless number that is often useful in analyzing fluid flows where there is an interface between two different fluids, such as multiphase flows with strongly curved surfaces (e.g., emulsions). The Weber number can be thought of as the relative importance of the fluid's inertia compared to its surface tension. The Weber number is the density of the fluid multiplied by the square of its velocity multiplied by the droplet diameter divided by the surface tension.

The Reynolds number is a dimensionless number that is a measure of the ratio of inertial forces to viscous forces. In some cases, the Reynolds number is calculated by multiplying the density of the fluid with the mean velocity of the object relative to the fluid times a characteristic linear dimension and dividing by the dynamic viscosity of the fluid.

In some examples, an individual droplet flows at Weber number of 1 or less. The Reynolds number of an individual droplet in an emulsion, or a plurality of droplets in the emulsion, may be less than about 2100, or in some cases greater than 2100. In some cases, the Reynolds number is between 0.1 and 1000.

In some examples, a droplet or emulsion comprising the droplet is heated by heating an oil in the carrier fluid reservoir such that the oil, upon flowing from the carrier fluid reservoir to the intersection, has a Reynolds number of at least about 1, 10, 1000, 2000, 3000, 4000, 5000 or higher.

This disclosure provides detection assemblies adapted to detect samples in droplets. A detection assembly may be adapted to detect an electromagnetic signal from the droplet. A detection assembly may be coupled to the detection channel. The detection channel may include a capillary for directing droplets to a detection region in communication with the detection assembly.

In some examples, the detection assembly includes an electromagnetic energy source and an electromagnetic energy detector, such as, for example, a fluorescence detector, which may be suited to detect fluorescence emissions from a droplet. The electromagnetic energy source and the electromagnetic energy detector may be used to irradiate, track, and analyze droplets. An electromagnetic energy detector may include a forward scatter detector. The electromagnetic energy source may provide excitation electromagnetic energy that has a frequency or range of frequencies for exciting an excitable species coupled to a sample in a droplet, such as a dye (e.g., fluorescence dye). The detection assembly can include optics (e.g., lenses, mirrors), which may direct the excitation electromagnetic energy to a droplet comprising a sample. Following excitation, the excitable species may emit an electromagnetic signal that may be detected by the electromagnetic energy detector. Optics may be provided for directing emitted electromagnetic energy to the detector.

Figure 4:
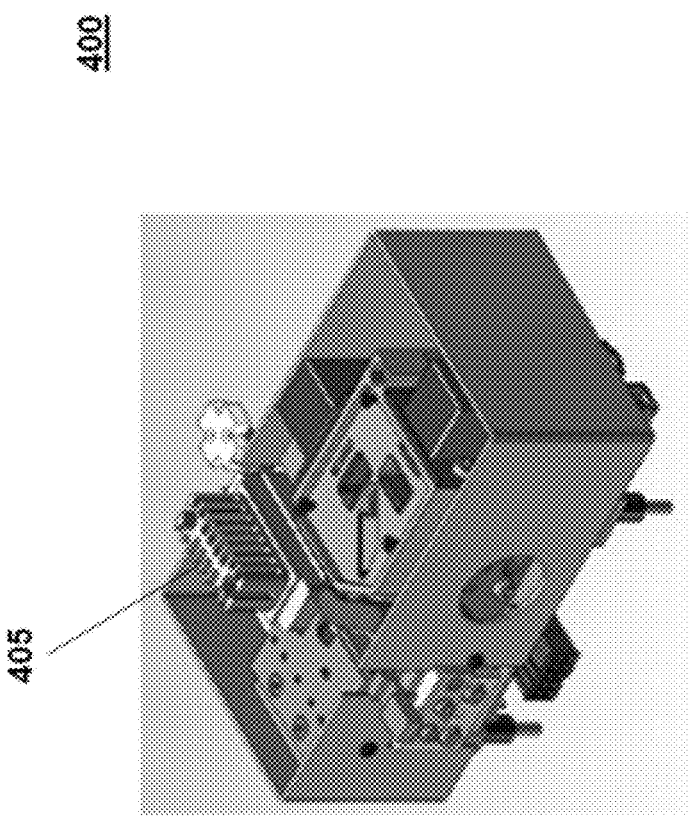
FIG. 4 schematically illustrates a detection assembly.

In some situations, a detection assembly may be configured to provide energy to an emulsion and/or droplet in the emulsion. FIG. 4 shows a detection assembly 400 comprising an energy application member 405. The detection assembly 400 can include one or a plurality of energy application members.

Figure 5:
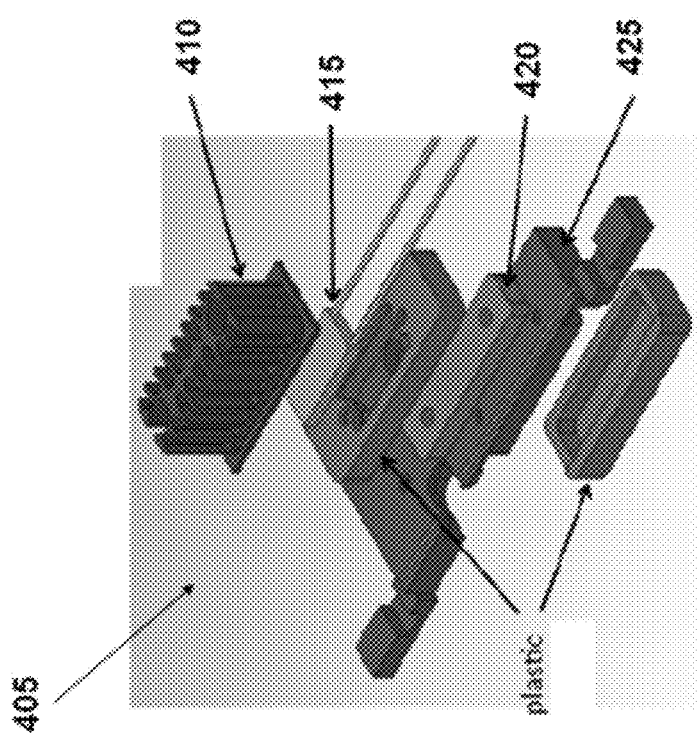
FIG. 5 schematically illustrates an exploded view of components of the detection assembly of FIG. 4.

FIG. 5 shows an exploded view of the energy application member 405. The energy application member 405 includes a heat sink 410, a thermoelectric module 415, a capillary clamp 420 and a modified plate with thermal breaks 425. The thermoelectric module 415 can include a thermoelectric heating element, such as, for example, a Peltier. As an alternative to the thermoelectric module 415, a resistive or infrared (IR) heating source may be used. The heat sink 410 can include heat fins that provide heat transfer areas to withdraw energy from the energy application member, which can provide cooling. The thermoelectric module 415 can provide energy for application to a fluid flowing through a fluid flow path in thermal communication with the energy application member. In some examples, the thermoelectric module 415 has a size of about 12 mm by 25 mm. In some cases, the capillary clamp 420 is metallic. Some of the components of the energy application member 405 may be formed of a polymeric material, such as plastic. In an example, some of the components of the energy application member 405 are formed of polytetrafluoroethylene (PTFE). The energy application member 405 illustrated in FIG. 5 may include additional components, such as thermal breaks and a thermistor.

Figure 7:
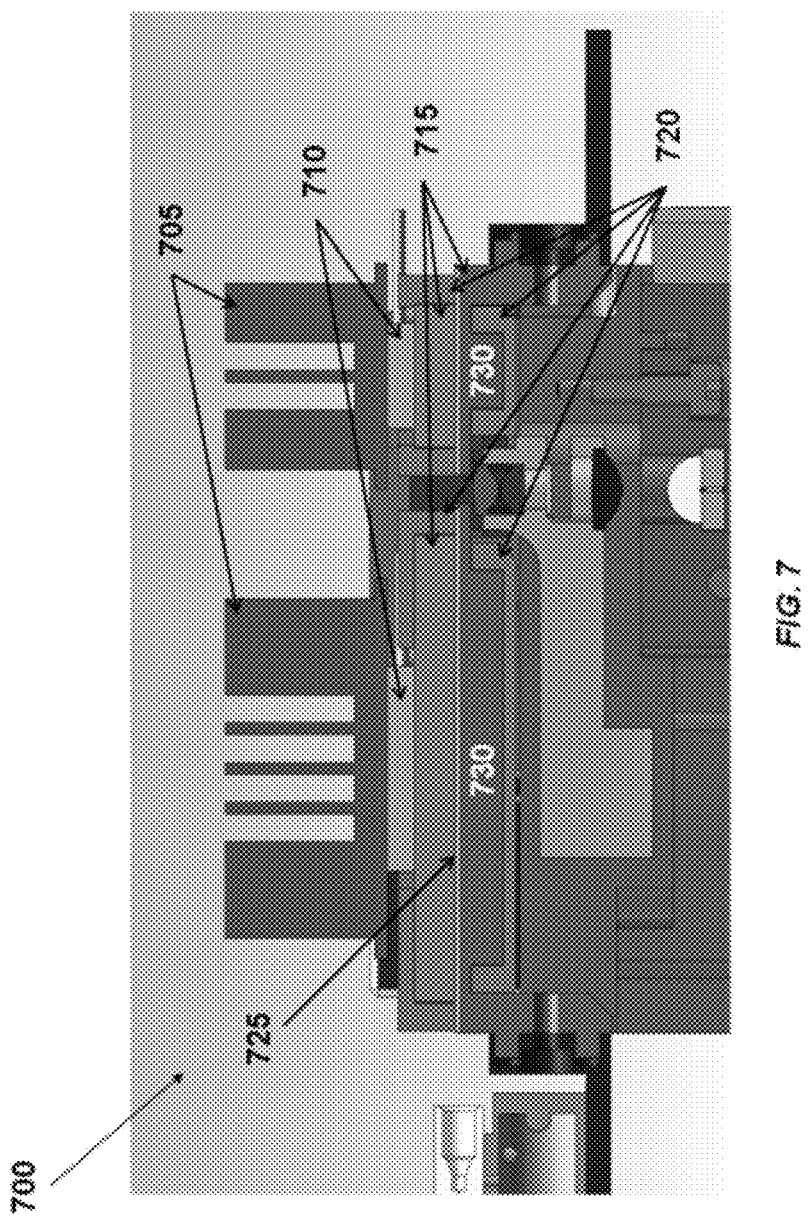
FIG. 7 schematically illustrates a detector that can be used to detect a signal in a droplet.

FIG. 7 schematically illustrates a detector 700 that can be used to detect a signal from a droplet. The detector 700 comprises heat sinks 705, thermoelectric devices 710, first metal blocks 715, insulation 720, a capillary groove 725 (or a plurality of capillary grooves), and second metal blocks 730. The capillary groove 725 can contain a fluid, such as, a flowing fluid. In an example, the capillary groove 725 contain one or more capillary tubes or channels in the capillary groove 725. The heat sinks 705 can be heat fins. The thermoelectric devices 710 can be thermoelectric heating devices, which can provide for heating. The first metal blocks 715 can be formed of aluminum or copper. The insulation 720 can be formed of a polymeric material, such as, for example, plastic. The second metal blocks 730 can be formed of aluminum or copper.

The detector 700 can include two heated segments to test the effect of heating lengths. In some examples, the flow of an emulsion through the capillary groove 725 can be reversed to switch between long and short segments.

A capillary tube or channel can be sandwiched between thermally-conductive blocks. In the illustrated example of FIG. 7, the detector 700 comprises a capillary tube in the capillary groove 725. The capillary tube can be sandwiched between an aluminum block and a copper block. During use, heat can flow from the thermoelectric devices 710 to the first metal blocks 715. Heat can then flow from the first metal blocks 715 to a capillary in the capillary groove 725, and subsequently to the second metal blocks 730.

In some situations, a thermally conductive material (e.g., silver paste) can be provided between the first metal blocks 715 and second metal blocks 730. The thermally conductive material can fill the capillary groove 725. The thermally conductive material can bring a capillary channel in the capillary groove 725 in thermal communication with the first metal blocks 715 and second metal blocks 730.

The temperature of an emulsion flowing through the capillary channel in the capillary groove 725 can be a function of the heating and/or cooling rates. Heating can be provided by the thermoelectric devices 710, and cooling can be provided by the heat sinks 705. In some situations, a resistive heater (or resistor) is provided adjacent to the heat sinks 705 to increase the heat flux through the thermoelectric devices 710.

In an example, with the device 700 a maximum temperature of about 50° C. is achieved for an emulsion flowing through the capillary channel in the capillary groove 725. If resistors adjacent to the heat sinks 705 are employed, temperatures greater than or equal to about 80° C. can be achieved.

Methods for Droplet Detection

Another aspect of the disclosure provides a method for analyzing a sample using a droplet detector (also "detection system" herein). The droplet detection may be as described elsewhere herein, such as the detection systems of FIG. 1, 2, 3A-3D, or 6. The method comprises providing an emulsion comprising a droplet. In some examples, the emulsion may be generated at an intersection of a first channel, a second channel and a detection channel. The first channel may be in fluid communication with a carrier fluid reservoir and the second channel may be in fluid communication with a sample reservoir. The emulsion may be formed upon the interaction of a carrier fluid from the carrier fluid reservoir with the sample (or sample partition) from the sample reservoir. Alternatively, the emulsion may already be provided upstream from the intersection, such as, for example, from the sample reservoir.

In some examples, the intersection is a singulator that receives a carrier fluid (e.g., focusing oil) and droplets from a sample reservoir comprising the droplets. The singulator can separate droplets prior to detection by a detection assembly.

The sample reservoir may comprise one or more droplets. An individual droplet may comprise a sample or sample partition, such as a nucleic acid sample.

The method may further comprise flowing the emulsion along the detection channel. The emulsion may flow to a collection reservoir or to a system or sub-system downstream of the detection channel, such as a detection assembly. As an alternative, the detection assembly can be coupled to at least a portion of the detection channel. The detection assembly may include a source of excitation energy and a detector for detecting a signal emitted from a droplet upon excitation with the excitation energy.

In some examples, a carrier fluid from a carrier fluid reservoir and droplet (or plurality of droplets) in a sample reservoir are induced to flow to the intersection with the aid of positive pressure supplied to the sample reservoir and/or the carrier fluid reservoir, or negative pressure (vacuum) supplied to the collection reservoir upstream of the intersection. An emulsion comprising the droplets may be formed at the intersection or may already be formed upstream from the intersection. In some cases, both positive and negative pressure are used to facilitate the flow of fluid to the intersection and subsequent flow of an emulsion comprising the droplet(s) to the collection reservoir. The emulsion is directed along a detection channel through a detection zone coupled to, or part of, a detection assembly. The droplet(s) and/or sample (or sample partition) are then detected with the aid of the detection assembly. The droplet(s) is then directed to the collection reservoir.

In some situations, upon flow of the emulsion along the detection channel, a signal from a droplet in the emulsion may be detected. The signal may be an electromagnetic (or optical), electrostatic, electrochemical, or magnetic signal. In some examples, an optical signal is detected. The optical signal may be from the droplet in a detection assembly in optical communication with at least a portion of the detection channel. The optical signal may be generated by directing excitation energy (e.g., excitation light) into the emulsion and detecting a signal emitted from the emulsion upon excitation. The signal may be a fluorescence signal from a dye associated with a sample or sample partition in a droplet, such as, for example, an intercalated dye.

The detection system may include a droplet generator upstream of the detection assembly. The droplet generator may be separately situated in relation to the detection assembly, such as in different systems. As an alternative, the droplet generator and the detection assembly (or droplet detector) are part of the same system and may be in fluid communication with one another.

In some cases, an emulsion may be energized (e.g., heated). As described elsewhere herein, the location of energy transfer to the emulsion (i.e., energy application zone) may be in the sample reservoir, carrier fluid reservoir, a channel emanating from a sample reservoir or carrier fluid reservoir, along at least a portion of the detection channel and/or at the intersection of the channels. In some cases, the carrier fluid is energized prior to generating an emulsion and/or the carrier fluid is energized after generating an emulsion. The emulsion can be heated along at least a portion of the detection channel with the aid of a heating member in thermal communication with the at least the portion of the detection channel. In an example, a droplet is heated in the detection assembly to improve the quality of signal detected. The droplets and/or emulsion may be heated to a temperature above the melting temperature of a non-specific target to eliminate or minimize the signal from a non-specific target in relation to the concentration of a specific target.

In some cases, a droplet is heated using a heating member in thermal communication with the sample (or droplet) reservoir, the carrier fluid reservoir, a channel emanating from the sample reservoir or carrier fluid reservoir, the intersection, at least a portion of the detection channel, the detection assembly, and/or the collection reservoir. Heating can be implemented with the aid of a resistive heating element, convective heating device, and/or radiative heating device. In an example, heat is applied with the aid of a resistive heating element in thermal communication with the detection channel and/or the intersection. In another example, heat is applied with the aid of an IR light source in optical communication with the detection channel and/or the intersection.

The emulsion may be heated to a uniform temperature. The emulsion may be heated to any suitable temperature (e.g., to a target temperature that is below the melting point of the sample or to a temperature below at which primer dimers form). In some examples, the emulsion is heated to a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 94° C., about 95° C., and the like. In some cases, the emulsion is heated to a temperature of at least about 20° C., at least about 25° C., at least about 30° C., at least about 35° C., at least about 40° C., at least about 45° C., at least about 50° C., at least about 55° C., at least about 60° C., at least about 65° C., at least about 70° C., at least about 75° C., at least about 80° C., at least about 85° C., at least about 90° C., at least about 94° C., or at least about 95° C. In other cases, the emulsion is heated to a temperature of at most about 20° C., at most about 25° C., at most about 30° C., at most about 35° C., at most about 40° C., at most about 45° C., at most about 50° C., at most about 55° C., at most about 60° C., at most about 65° C., at most about 70° C., at most about 75° C., at most about 80° C., at most about 85° C., at most about 90° C., at most about 94° C., at most about 95° C., at most about 100° C., at most about 105° C., at most about 110° C., at most about 115° C., or at most about 120° C.

The droplets may be heated to a uniform temperature. The droplets can be heated to any suitable temperature (e.g., to a target temperature that is below the melting point of the sample or to a temperature below at which primer dimers form). In some examples, the droplets are heated to a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 94° C., about 95° C., and the like. In some cases, the droplets are heated to a temperature of at least about 20° C., at least about 25° C., at least about 30° C., at least about 35° C., at least about 40° C., at least about 45° C., at least about 50° C., at least about 55° C., at least about 60° C., at least about 65° C., at least about 70° C., at least about 75° C., at least about 80° C., at least about 85° C., at least about 90° C., at least about 94° C., or at least about 95° C. In other cases, the droplets are heated to a temperature of at most about 20° C., at most about 25° C., at most about 30° C., at most about 35° C., at most about 40° C., at most about 45° C., at most about 50° C., at most about 55° C., at most about 60° C., at most about 65° C., at most about 70° C., at most about 75° C., at most about 80° C., at most about 85° C., at most about 90° C., at most about 94° C., or at most about 95° C. The droplets may be heated to a uniform temperature between about 25° C. and 90° C.

The droplets and/or emulsion may be heated to a temperature above the melting temperature of a non-specific target. A non-specific target includes, but is not limited to, any molecular binding event that is not a nucleic acid base pairing. Non-specific targets also include primer-dimer pairs.

The droplets may be heated to a temperature below the melting temperature of a specific target. Specific targets include, but are not limited to, nucleic acid base pairing interactions. In some embodiments, the specific target is a nucleic acid. In some cases, the specific target is an amplicon (e.g., a nucleic acid formed as the product of an amplification event such as PCR).

The droplets may be heated to a temperature at which a dye binds to a nucleic acid (e.g., DNA). Intercalating dyes can be used. Examples of intercalating dyes are ethidium bromide, SYBR Green™, SYBR Gold™, 4',6-diamidino-2-phenylindole (DAPI), EVA Green™ or any combination thereof. In some embodiments, the droplets are heated to a temperature at which a dye binds to a sample and/or RNA.

The sample may comprise a nucleic acid (e.g., DNA, RNA). The droplet and/or the emulsion can be heated to induce nucleic acid amplification in the droplet (e.g., prior to detection). In some cases, the emulsion is heated along a temperature gradient (e.g., where the temperature increases along the detection channel).

Energy may be provided from various types of energy sources and through various types of energy transfer. For example, energy can be provided as thermal energy (e.g., heat, conduction, convection, radiation, or a combination thereof), electromagnetic energy (e.g., gamma rays, x-rays, ultraviolet rays, visible light, infrared rays, microwaves, radio waves, or any combination thereof), electrical energy, chemical energy, mechanical energy, or any combination thereof. In some cases, the energy is transformed to thermal energy (i.e., heat).

For example, energy can be provided by one or more heating elements. The one or more heating elements can comprise a resistive heating element, a thermoelectric device, a heating block, a lamp, a light source, a microwave, a radiation source, a water bath, or any combination thereof.

There can be a plurality of heating elements. In some embodiments, a first heating element provides a first amount of energy and a second heating element provides a second amount of energy. The heating elements can be used to cycle the temperature (e.g., for performing polymerase chain reaction (PCR), real-time PCR, and the like).

In some examples, energy may be provided to provide droplet stability and/or induce nucleic acid amplification prior to detection. A first quantity of energy may stabilize a droplet (e.g., by forming a skin on the droplets and/or preventing two or more droplets from coalescing) and a second quantity of energy may initiate a reaction within the droplets. The reaction can be any type of PCR, isothermal nucleic acid amplification, in-vitro translation, or a combination thereof.

A droplet may flow through a detection channel at any suitable rate. The flow rate is equal to droplets per time multiplied by the average droplet volume. In some examples, one or more droplets flow at a rate of about 0.1, about 0.5, about 1, about 5, about 10, about 50, about 100, about 500, about 1000, about 5000, about 10000, or about 50000 µl/minute. In some cases, one or more droplets flow at a rate of at least about 0.1, at least about 0.5, at least about 1, at least about 5, at least about 10, at least about 50, at least about 100, at least about 500, at least about 1000, at least about 5000, at least about 10000, or at least about 50000 µl/minute. One or more droplets may flow at a rate of between 0.5 µl/minute and 10000 µl/minute, or between 1 µl/minute and 5000 µl/minute. Energy may be provided to one or more droplets under flow.

The Weber number associated with the emulsion directed through the detection channel may be about 0.01, about 0.05, about 0.1, about 0.5, about 1, or about 5. In some cases, the Weber number is at least about 0.01, at least about 0.05, at least about 0.1, at least about 0.5, at least about 1, or at least about 5. In some situations, the Weber number may be at most about 0.01, at most about 0.05, at most about 0.1, at most about 0.5, at most about 1, or at most about 5.

In some instances, the flow through the detection channel is laminar (e.g., has a Reynolds number that is less than about 2100). In some instances, the flow is turbulent (e.g., has a Reynolds number that is greater than about 2100). In some embodiments, the Reynolds number is about 0.05, about 0.1, about 0.5, about 1, about 5, about 10, about 50, about 100, about 500, about 1000, about 5000 or about 10000. In some embodiments, the Reynolds number is at least about 0.05, at least about 0.1, at least about 0.5, at least about 1, at least about 5, at least about 10, at least about 50, at least about 100, at least about 500, at least about 1000, at least about 5000 or at least about 10000. In some embodiments, the Reynolds number is at most about 0.05, at most about 0.1, at most about 0.5, at most about 1, at most about 5, at most about 10, at most about 50, at most about 100, at most about 500, at most about 1000, at most about 5000 or at most about 10000. In some embodiments, the Reynolds number is between 0.1 and 1000.

In some cases, as a droplet flows from the intersection to the collection reservoir or a detection region along the detection channel, the temperature of the detection channel may be cycled to induce nucleic acid amplification. This can advantageously enable in-line nucleic acid amplification prior to sample detection. In some cases, prior to temperature cycling, the droplet is heated to induce skin formation around the droplet.

In some cases, droplets are exposed to a sequence of temperatures to enable a PCR reaction (e.g., a denaturation temperature, an annealing temperature, and an extension temperature) prior to detection. The temperatures may be optimized for a particular assay. Examples of temperatures may be from about 94° C. to 96° C. Examples of annealing temperatures may be from about 37° C. to 75° C. Examples of extension temperatures may be from about 60° C. to 72° C. In some cases, the droplets are exposed to temperature to enable hot-start of an enzyme, such as a polymerase. An example temperature for enabling hot-start is about 95° C.

In some situations, a droplet is stabilized by heating (e.g., incubating) the droplet at a temperature between about 4° C. and 99° C., or 30° C. and 80° C., or 50° C. and 65° C. for at least 0.1, 1, 2, 3, 4, 5, 6, 7, 8, 9, 10, 20, 30, 40, 50, 60, 70, 80, 90, 100, 200, 300, 400, 500, or 1000 seconds. In some examples, the droplet may be stabilized by heating the droplet at a temperature between about 50° C. and 65° C. for 5 or more seconds. In other examples, the droplet is stabilized by heating the droplet at a temperature between about 30° C. and 80° C. for a time period between about 5 seconds and 2 hours. In other examples, the droplet is stabilized by heating the droplet at a temperature between about 80° C. and 95° C. for a time period between about 5 seconds and 30 minutes.

During or prior to detection, a droplet may be heated along a temperature gradient. The temperature gradient may have a first temperature at a first portion of the detection channel and a second temperature at a second portion of the detection channel downstream of the first portion. The temperature gradient can have temperatures from about 55° C. and 98° C. In an example, the temperature at the first portion is 55° C. and the temperature at the second portion is 75° C., and the temperature from the first portion to the second portion is increased (e.g., gradually increased) from 55° C. to 75° C. Alternatively, the droplet can be heated at a constant temperature for a time sufficient to minimize or eliminate the signal generated from a non-specific target. In an example, the droplet is heated at a temperature from about 55° C. and 98° C. for a time period from about 1 second to 15 minutes.

In some cases, methods may include the detection of a nucleic acid in a sample. Such methods may comprise (a) providing a sample comprising a plurality of partitions, wherein at least one of the partitions comprises an amplified nucleic acid, and (b) detecting an optical signal from at least one of the partitions, wherein the temperature of the partition is at least 50° C. The optical signal can be correlated with an amount of the nucleic acid.

Devices, systems and methods of the disclosure may be combined with or modified by other devices, systems and methods, such as, for example, those described in U.S. Patent Publication No. 2010/0173394 to Colston et al. ("Droplet-based assay system"), which is entirely incorporated herein by reference for all purposes.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of embodiments of the invention herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A method of analyzing a sample including a nucleic acid target, the method comprising:

introducing droplets of an emulsion into a detection device from a reservoir, wherein the detection device includes a channel intersection upstream of a detection channel, wherein the detection channel comprises a capillary, and wherein each droplet of only a subset of the droplets being introduced contains a nucleic acid target that has been amplified in the subset;

adding carrier fluid at the channel intersection to increase separation between the droplets;

heating droplets within the detection channel; and detecting a signal for amplification of the nucleic acid target from heated droplets flowing along the detection channel.

2. The method of claim 1, wherein the step of heating droplets includes a step of heating droplets to a temperature of at least about 40° C.

3. The method of claim 1, wherein the step of heating droplets includes a step of heating droplets to a temperature of at least about 50° C.

4. The method of claim 1, wherein the step of heating droplets includes a step of heating droplets to a temperature that is above the melting point of a non-specific target in the sample and below the melting point of the nucleic acid target.

5. The method of claim 1, wherein the step of introducing droplets includes a step of introducing droplets having a skin around each of the droplets, and wherein the skin comprises protein.

6. The method of claim 1, wherein the nucleic acid target has been amplified in the subset of droplets while the subset is disposed in the reservoir and while the reservoir is off-line from the detection channel.

7. The method of claim 1, wherein the step of introducing droplets includes a step of pipetting droplets into the detection device from the reservoir.

8. The method of claim 1, further comprising a step of forming the emulsion separately and off-line from the detection device.

9. The method of claim 1, wherein droplets of the emulsion include an intercalating dye or a labeled oligonucleotide probe.

* * * * *